(12) United States Patent
Ono et al.

(10) Patent No.: US 11,226,419 B2
(45) Date of Patent: Jan. 18, 2022

(54) RADIATION DETECTING DEVICE, RADIATION DETECTING SYSTEM, AND METHOD FOR MANUFACTURING THE RADIATION DETECTING DEVICE

(71) Applicant: CANON KABUSHIKI KAISHA, Tokyo (JP)

(72) Inventors: Shinji Ono, Honjo (JP); Takamasa Ishii, Honjo (JP); Kota Nishibe, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 28 days.

(21) Appl. No.: 16/794,731

(22) Filed: Feb. 19, 2020

(65) Prior Publication Data

US 2020/0183022 A1    Jun. 11, 2020

Related U.S. Application Data (63) Continuation of application No. 15/103,247, filed as application No. PCT/JP2014/078874 on Oct. 30, 2014, now abandoned.

(30) Foreign Application Priority Data

Dec. 13, 2013  (JP) .................................. 2013-258139

(51) Int. Cl.
  *G01T 1/20*       (2006.01)
  *H01L 27/146*     (2006.01)
  *A61B 6/00*       (2006.01)

(52) U.S. Cl.
  CPC ............ *G01T 1/2018* (2013.01); *A61B 6/461* (2013.01); *A61B 6/486* (2013.01); *H01L 27/14663* (2013.01)

(58) Field of Classification Search
  CPC .... A61B 6/486; A61B 6/461; H01L 27/14663
  See application file for complete search history.

(56) References Cited

U.S. PATENT DOCUMENTS

| 2002/0159563 A1* | 10/2002 | Tashiro | ................. G01T 1/2018 |
| | | | 378/98.8 |
| 2003/0062481 A1* | 4/2003 | Okada | .................... G01T 1/202 |
| | | | 250/361 R |
| 2013/0026380 A1* | 1/2013 | Tkaczyk | ............... G01T 1/2928 |
| | | | 250/370.13 |

OTHER PUBLICATIONS

Safavi Naeini et al. Evaluation of silicon detectors with integrated JFET for biomedical applications, IEEE Transactions on Nuclear Science, vol. 56, No. 3, pp. 1051-1055 (Year: 2009).*

* cited by examiner

*Primary Examiner* — David P Porta
*Assistant Examiner* — Shun Lee
(74) *Attorney, Agent, or Firm* — Canon U.S.A., Inc. IP Division (57) ABSTRACT

A radiation detecting device in which defective adhesion between an adhesive member and end portions of a plurality of sensor substrates is reduced.

A radiation detecting device includes a plurality of sensor substrates disposed adjacent to each other, each sensor substrate including a side surface that connects a first surface, where a plurality of photoelectric converting elements are arranged in an array, and an opposing second surface to each other; a scintillator disposed at a side of the first surfaces of the plurality of sensor substrates; and a sheet-like adhesive member for adhering the plurality of sensor substrates and the scintillator to each other, wherein, between the plurality of sensor substrates, the sheet-like adhesive member adheres to the first surfaces and at least portions of the side surfaces such that the sheet-like adhesive

(Continued)

member extends and continuously adheres from the first surfaces to the at least portions of the side surfaces.

10 Claims, 6 Drawing Sheets

RADIATION DETECTING DEVICE, RADIATION DETECTING SYSTEM, AND METHOD FOR MANUFACTURING THE RADIATION DETECTING DEVICE

CROSS-REFERENCE TO RELATED APPLICATIONS

This is a continuation application of U.S. patent application Ser. No. 15/103,247 filed on Jun. 9, 2016 which is a National Phase Application of PCT/JP2014/078874 filed on Oct. 30, 2014 which claims priority from Japanese Patent Application No. 2013-258139 filed Dec. 13, 2013, all of which are incorporated herein in their entirety.

TECHNICAL FIELD

The present invention relates to a radiation detecting device that detects radiation, a radiation detecting system that uses the radiation detecting device, and a method for manufacturing the radiation detecting device.

BACKGROUND ART

For a radiation detecting device, a so-called indirect conversion radiation detecting device including a sensor substrate where a plurality of photoelectric converting elements are arranged in an array, and a scintillator that converts radiation into light that is detectable by the photoelectric converting elements may be used.

In order to provide a radiation detecting device having a large area, PTL 1 discloses a radiation detecting device in which a plurality of sensor substrates are disposed adjacent to each other and a scintillator is disposed so as to extend over the plurality of sensor substrates. PTL 1 discloses a radiation detecting device in which the plurality of sensor substrates and the scintillator are adhered to each other by an adhesive member.

CITATION LIST

Patent Literature

PTL 1: Japanese Patent Laid-Open No. 2012-007948

SUMMARY OF INVENTION

Technical Problem

However, in the radiation detecting device described in PTL 1, there is room for considering the adhesive strength of the adhesive member that is positioned between the plurality of sensor substrates. When the adhesive member that is positioned between the plurality of sensor substrates is peeled from the plurality of sensor substrates due to, for example, temperature variations and vibration, a gap may be formed between the adhesive member and end portions of the plurality of sensor substrates. In the gap and the adhesive member, differences in states of propagation of light from the scintillator to the sensor substrates occur. These differences may cause artifacts to occur in images acquired from the plurality of sensor substrates.

Solution to Problem

Accordingly, the present invention provides a radiation detecting device in which defective adhesion between an adhesive member and end portions of a plurality of sensor substrates is reduced.

A radiation detecting device according to the present invention includes a plurality of sensor substrates disposed adjacent to each other, each sensor substrate including a first surface where a plurality of photoelectric converting elements are arranged in an array, a second surface that opposes the first surface, and a side surface that connects the first surface and the second surface to each other; a scintillator disposed at a side of the first surfaces of the plurality of sensor substrates; and a sheet-like adhesive member for adhering the plurality of sensor substrates and the scintillator to each other, wherein, between the plurality of sensor substrates, the sheet-like adhesive member adheres to the first surfaces and at least portions of the side surfaces such that the sheet-like adhesive member extends and continuously adheres from the first surfaces to the at least portions of the side surfaces.

A method for manufacturing a radiation detecting device according to the present invention includes a disposing step of disposing a scintillator at a side of first surfaces of a plurality of sensor substrates with a sheet-like adhesive member interposed therebetween, the plurality of sensor substrates being disposed adjacent to each other, each sensor substrate including the first surface where a plurality of photoelectric converting elements are arranged in an array, a second surface that opposes the first surface, and a side surface that connects the first surface and the second surface to each other; and an adhering step of causing the sheet-like adhesive member to extend and continuously adhere from the first surfaces to at least portions of the side surfaces between the plurality of sensor substrates by pressing a region of the scintillator corresponding to a region between the plurality of sensor substrates from a side opposite to the plurality of sensor substrates.

DESCRIPTION OF EMBODIMENTS

Embodiments according to the present invention are hereunder described below in detail with reference to the drawings. In the various embodiments, corresponding components are given the same reference numerals, and the same descriptions thereof are not given. In the present invention, light includes visible light and infrared light, and radiation includes X rays, α rays, β rays, and γ rays.

First, an exemplary general structure of a radiation detecting device 100 according to an embodiment is described by using FIGS. 1(a) to 1(c). FIG. 1(a) is a schematic plan view for describing the radiation detecting device 100. FIG. 1(b)

is a schematic sectional view for describing a sectional structure at a portion along A-A' in FIG. 1(a). FIG. 1(c) is an enlarged schematic sectional view of a region B in FIG. 1(b).

As shown in FIGS. 1(a) to 1(c), the radiation detecting device 100 according to the embodiment includes a plurality of sensor substrates 112, a scintillator 120, and an adhesive member 130. Each of the plurality of sensor substrates 112 includes a first surface 112a where a plurality of photoelectric converting elements 115 are arranged in an array, a second surface 112b that opposes the first surface 112a, and a side surface 112c that connects the first surface 112a and the second surface 112b to each other. The plurality of sensor substrates 112 are disposed adjacent to each other. The scintillator 120 is disposed at a side of the first surfaces of the plurality of sensor substrates 112. The adhesive member 130 adheres the plurality of sensor substrates 112 and the scintillator 120 to each other at the side of the first surfaces of the plurality of sensor substrates 112. Here, between the plurality of sensor substrates 112, the sheet-like adhesive member 130 adheres to at least portions of the side surfaces 112c and the first surfaces 112a such that the sheet-like adhesive member 130 extends and continuously adheres from the first surfaces 112a to at least portions of the side surfaces 112c. That is, the adhesive member 130 adheres the plurality of sensor substrates 112 and the scintillator 120 to each other, and is provided so as to extend from the first surfaces 112a to at least portions of the side surfaces 112c of the sensor substrates 112. By such an adhesion, even if changes occur in the adhesive member 130 due to temperature loads and vibration loads, defective adhesion of the adhesive member 130 with respect to the plurality of sensor substrates 112 is reduced. In addition, the occurrence of gaps between the adhesive member 130 and the plurality of sensor substrates 112 is reduced, so that the occurrence of image artifacts caused thereby is reduced.

At each sensor substrate 112, the plurality of photoelectric converting elements 115 are arranged in an array at the first surface 112a. In the embodiment, for each sensor substrate 112, a monocrystalline silicon substrate manufactured from a monocrystalline silicon wafer is used, with a photodiode being used as each photoelectric converting element 115. A plurality of switching elements (not shown) corresponding to the plurality of photoelectric converting elements 115 may be provided at each sensor substrate 112. The sensor substrates 112 according to the present invention are not limited to the above-described substrates. Sensor substrates that are provided with TFT pixels and an MIS sensor or a PIN sensor using, for example, amorphous silicon deposited on an insulating board may be used. Further CCD or SOI (silicon-on-insulator) sensors may be used. Each sensor substrate 112 according to the embodiment further includes a guard ring 118, a passivation film 116, and a protective layer 117. The guard rings 118 are conductors that are provided for preventing electro-static damage to the photoelectric converting elements 115. Each guard ring 118 is disposed on at least a portion of the corresponding first surface 112a along peripheries of the plurality of photoelectric converting elements 115. Each passivation film 116 is an insulating film that covers the photoelectric converting elements 115. For each passivation film 116, an inorganic insulating film, such as a silicon oxide film or a silicon nitride film, is suitably used.

Each passivation film 116 covers a portion of the guard ring 118 and the plurality of photoelectric converting elements 115. Each protective layer 117 is a layer for protecting the photoelectric converting elements 115 and its corresponding passivation film 116 from, for example, external shock. For each protective layer 117, an organic insulating layer, such as a polyimide layer, is suitably used. Each protective layer 117 covers its corresponding passivation film 116 excluding an end portion of its corresponding passivation film 116.

The scintillator 120 converts X rays, which are radiation rays, transmitted through a test object into light having wavelengths that are detectable by the photoelectric converting elements 115 of the sensor substrates 112. The scintillator 120 according to the embodiment includes a base material 121, a scintillator layer 122, and a scintillator protective layer 123. Although, for the base material 121, for example, a-C, Al, or a resin may be used, Al that is less rigid than a-C may be suitably used. The scintillator layer 122 is a layer that converts X rays into light having wavelengths that are detectable by the photoelectric converting elements 115. For the scintillator layer 122, GOS or CsI:Tl may be used. GOS is $Gd_2O_2S$:Tb (terbium-doped gadolinium oxysulfide), and is a granular scintillator material. CsI:Tl typifies alkali halide based scintillators, and is thallium-doped cesium iodide, and includes scintillator materials containing columnar crystals. The scintillator protective layer 123 is a layer that protects the scintillator layer 122 from external moisture and external shock. For the scintillator protective layer 123, an organic resin, such as a polyparaxylylene resin or a hot-melt resin, may be suitably used. For simplifying FIG. 1(b), the protective layer 123 is not shown.

The adhesive member 130 adheres the plurality of sensor substrates 112 and the scintillator 120 to each other at the side of the first surfaces of the plurality of sensor substrates 112. Here, between the plurality of sensor substrates 112, the adhesive member 130 adheres to at least portions of the side surfaces 112c and the first surfaces 112a such that the adhesive member 130 extends and continuously adheres from the first surfaces 112a to at least portions of the side surfaces 112c. In the embodiment, between the plurality of sensor substrates 112, the adhesive member 130 extends on and continuously adheres to the protective layers 117, the passivation films 116, the guard rings 118, the first surfaces 112a of the sensor substrates 112, and at least portions of the side surfaces 112c of the sensor substrates 112. In this way, by causing the sheet-like adhesive member 130 to extend on and continuously adhere to a structure having a stepped surface, the adhesive member 130 more suitably adheres to the sensor substrates 112. For the adhesive member 130, a material having a high light transmittance with respect to light converted by the scintillator 120 is suitably used. For example, a sheet-like member, such as an acrylic resin sheet, a silicon-based resin sheet, or a hot-melt resin sheet, may be suitably used. It is desirable that the adhesive member 130 contain an organic resin whose adhesive strength with respect to glass when the peeling angle in conformity with JIS 20237 is 180 degrees is 10 N/25 mm or greater, whose transmittance with respect to the maximum emission wavelength of the scintillator is 90% or greater, and whose thickness is from 1 μm to 50 μm.

A base 111 is a member that mechanically supports the plurality of sensor substrates 112. For the base 111, a base, such as a glass substrate or an SUS substrate, having a rigidity that is higher than those of the base material 121 and the scintillator layer 122 is suitably used. A fixing member 113 is a member having adhesiveness for fixing the plurality of sensor substrates 112 to the base 111. For the fixing member 113, a material that is the same as that used for the adhesive member 130 may be used. Wiring boards 114 are wiring boards for transmitting signals between an external circuit (not shown) and the sensor substrates 112. For the wiring boards 114, flexible printed boards may be used.

Figure 1:
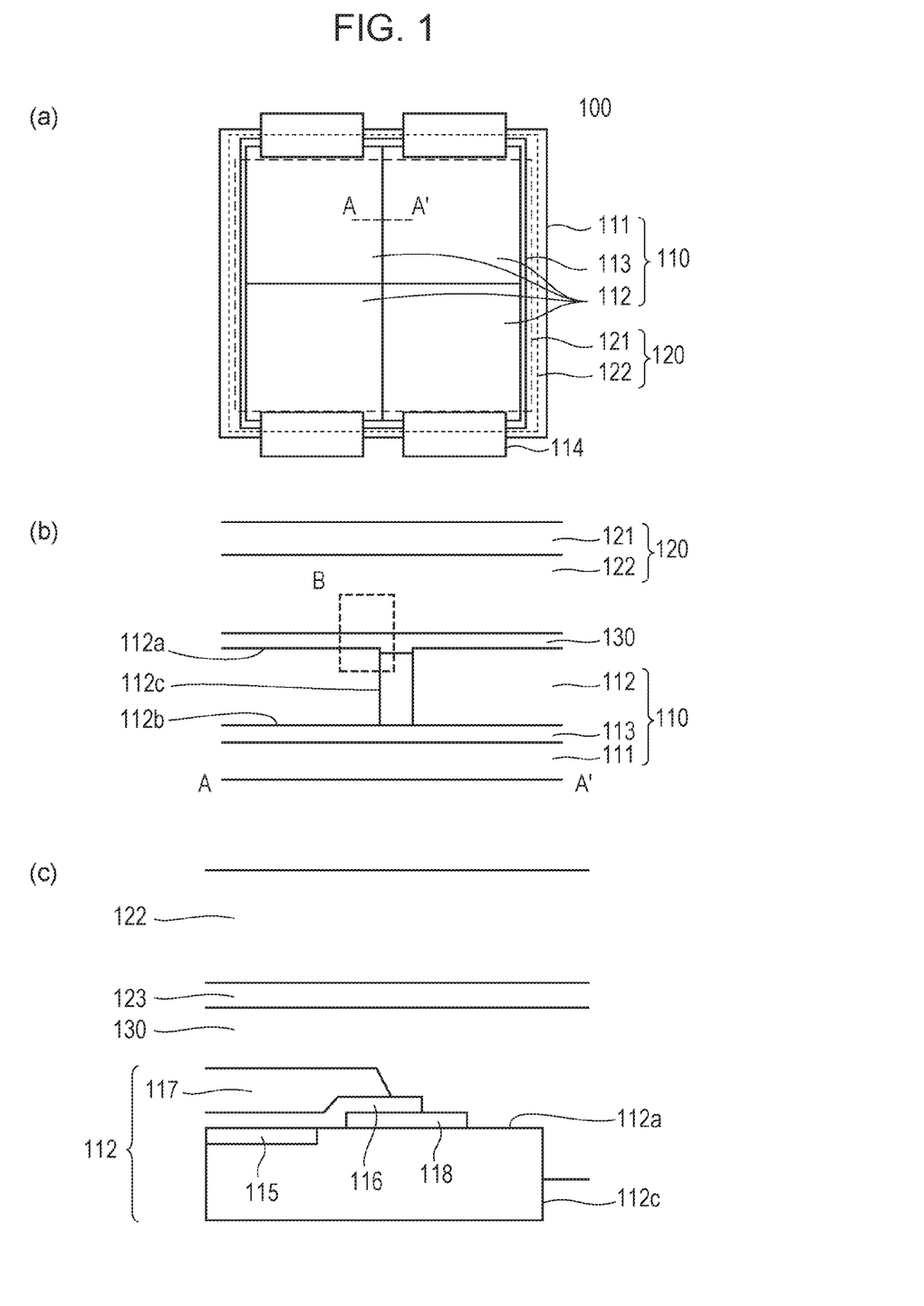
FIG. 1 is a schematic plan view, a schematic sectional view, and an enlarged schematic sectional view for describing a radiation detecting device.
Figure 2:
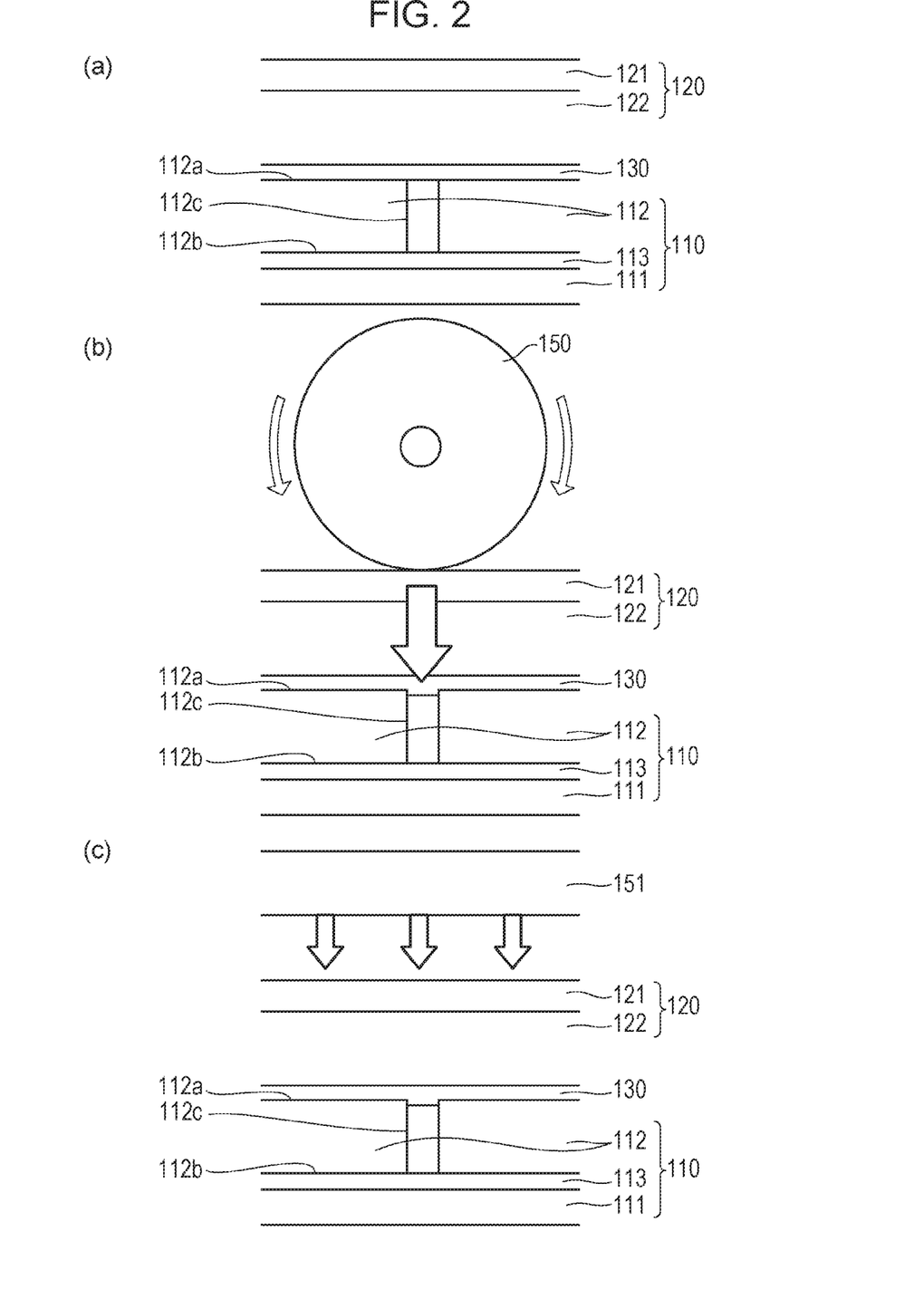
FIG. 2 is a schematic sectional view for describing a method for manufacturing the radiation detecting device.

Next, a method for manufacturing the radiation detecting device 100 according to this embodiment is described by using FIGS. 2(*a*) to 2(*c*). FIG. 2(*a*) is a schematic sectional view for describing a sectional structure prior to an adhering step at a portion corresponding to the portion along A-A' in FIG. 1(*a*). FIG. 2(*b*) is a schematic sectional view that describes an exemplary adhering step. FIG. 2(*c*) is a schematic sectional view for describing another exemplary adhering step. For simplifying FIGS. 2(*a*) to 2(*c*), the protective layer 123 is not shown.

First, as shown in FIG. 2(*a*), by performing a fixing step of fixing the second surfaces 112*b* of the plurality of sensor substrates 112 to the base 111 by using the fixing member 113, the plurality of sensor substrates 112 are disposed on the base 111. By a disposing step of disposing the scintillator 120 including the scintillator layer 122, provided on the base material 121, at the side of the first surfaces of the plurality of sensor substrates 112 with the adhesive member 130 interposed therebetween, the scintillator layer 122 is disposed on the surfaces 112*a* of the plurality of sensor substrates 112.

Next, as shown in FIG. 2(*b*), a region of the scintillator 120 corresponding to a region between the plurality of sensor substrates 112 is pressed from a side opposite to the plurality of sensor substrates 112. In the method shown in FIG. 2(*b*), a rotatable roller 150 linearly presses the adhesive member 130 along a side opposing the sensor substrates 112 from the side opposite to the plurality of sensor substrates 112. In this way, by pressing the region of the scintillator 120 corresponding to the region between the plurality of sensor substrates 112, regions of portions of the adhesive member 130 that are positioned between the plurality of sensor substrates 112 also adhere to regions of portions of the side surfaces 112*c* of the sensor substrates 112. It is desirable that the pressure generated by the roller 150 be greater than or equal to 0.4 MPa.

As shown in FIG. 2(*c*), when a hot-melt resin is used as the adhesive member 130, the region of the scintillator 120 corresponding to the region between the plurality of sensor substrates 112 may be pressed from the side opposite to the plurality of sensor substrates 112 by using a pressure structure 151 whose temperature is adjustable. When, by the pressure structure 151, the hot-melt resin is heated to a temperature that is greater than or equal to the melting temperature, and is pressed at a pressure that is greater than or equal to 0.4 MPa, the regions of the portions of the adhesive member 130 that are positioned between the plurality of sensor substrates 112 also adhere to the regions of the portions of the side surfaces 112*c* of the sensor substrates 112.

Figure 3:
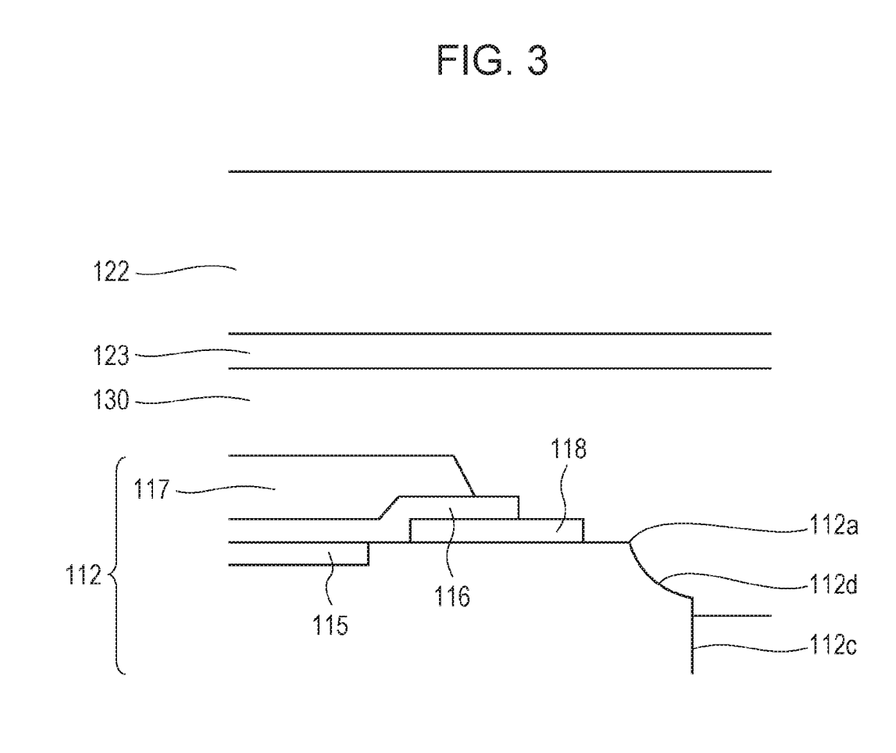
FIG. 3 is a schematic sectional view for describing a radiation detecting device according to a different embodiment.

The side surfaces 112*c* of the plurality of sensor substrates 112 may have various structures for increasing the adhesive strength of the adhesive member 130. An exemplary structure for increasing the adhesive strength of the adhesive member 130 is shown in FIG. 3. FIG. 3 is a schematic sectional view for describing the exemplary structure for increasing the adhesive strength of the adhesive member 130 in an enlarged sectional structure of a region B in FIG. 1(*b*). In the example shown in FIG. 3, corners that may form the surfaces 112*a* and the side surfaces 112*c* of the sensor substrates 112 are removed, so that third surfaces 112*d* that are not parallel to the first surfaces 112*a* and the side surfaces 112*c* are provided between the first surfaces 112*a* and the side surfaces 112*c* of the sensor substrates 112. The adhesive member 130 extends on and continuously adheres to at least portions of the side surfaces 112*c* and the third surfaces 112*d* from the first surfaces 112*a* between the plurality of sensor substrates 112. By virtue of such a structure, the adhesive member 130 is capable of suitably continuously covering portions up to the side surfaces 112*c*. By increasing the adhesion area, the adhesive strength of the adhesive member 130 is also increased.

Figure 4:
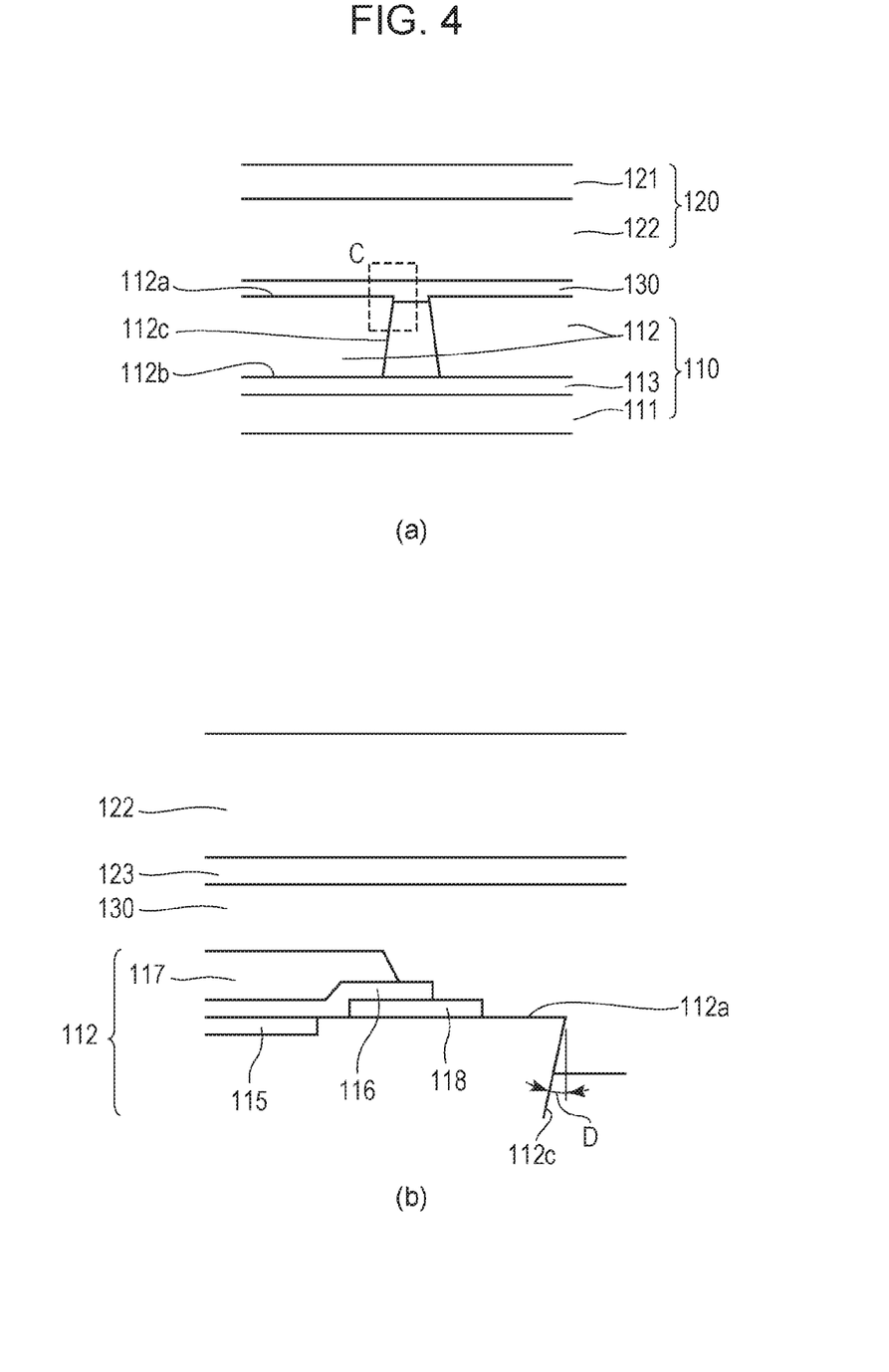
FIG. 4 is a schematic sectional view and an enlarged schematic sectional view for describing a radiation detecting device according to a different embodiment.

FIGS. 4(*a*) and 4(*b*) each show a different exemplary structure for increasing the adhesive strength of the adhesive member 130. FIG. 4(*a*) is a schematic sectional view for describing a sectional structure of the different exemplary structure for increasing the adhesive strength of the adhesive member 130 at a portion along A-A' in FIG. 1(*a*). FIG. 4(*b*) is an enlarged schematic sectional view of a region C in FIG. 4(*a*). For simplifying FIG. 4(*a*), the protective layer 123 is not shown. In the different exemplary structure shown in FIGS. 4(*a*) and 4(*b*), the side surface 112*c* of at least one of the plurality of sensor substrates 112 is inclined. The inclination extends towards an inner side of the sensor substrate 112 at an angle D from the first surface 112*a* towards the second surface 112*b* with respect to a perpendicular line that is perpendicular to the first surface 112*a*. Between the plurality of sensor substrates 112, a structure that is inclined at such an angle D is provided, so that this structure is one in which the adhesive member 130 is less likely to peel from at least a portion of the side surface 112*c* compared to the structure in FIG. 1(*c*). It is desirable that the angle D be from 0.2 degrees to 5 degrees.

Figure 5:
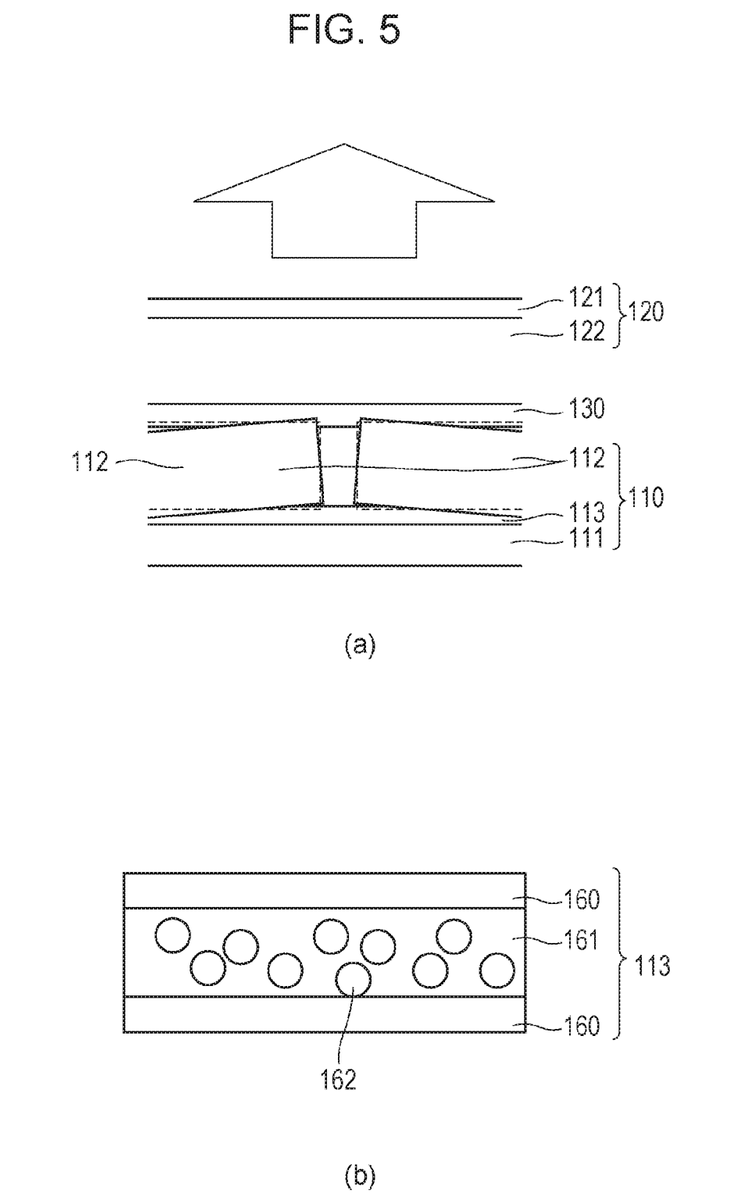
FIG. 5 is a schematic sectional view of a radiation detecting device according to a different embodiment.

It is desirable that the rigidity of the fixing member 113 be lower than the rigidity of the adhesive member 130. By using FIGS. 5(*a*) and 5(*b*), a radiation detecting device using a more desirable fixing member 113 is described. FIG. 5(*a*) is a schematic sectional view for describing a sectional structure of the radiation detecting device using the more desirable fixing member 113. FIG. 5(*b*) is a schematic sectional view for describing the more desirable fixing member 113. As shown in FIG. 5(*a*), since the rigidity of the fixing member 113 is lower than the rigidity of the adhesive member 130, even if stress caused by temperature variations and differences between thermal expansion coefficients occurs, the fixing member 113 absorbs this stress. Therefore, the stress that is applied to the adhesive member 130 is reduced, and the intrusion of air bubbles into the adhesive member 130 due to peeling of the adhesive member 130 from the first surfaces 112*a* of the plurality of sensor substrates 112 is reduced. As the desirable fixing member 113, as shown in FIG. 5(*b*), a sheet-like fixing member 113 including an expanding-and-contracting material 161 that is sandwiched by an adhesive member 160 is available. As the expanding-and-contracting material 161, a sheet-like polyolefin-based foam is used, and air bubbles 162 are contained in the expanding-and-contracting material 161. As the adhesive member 160, for example, a sheet-like acrylic adhesive member or a sheet-like silicon-based adhesive member is used.

Figure 6:
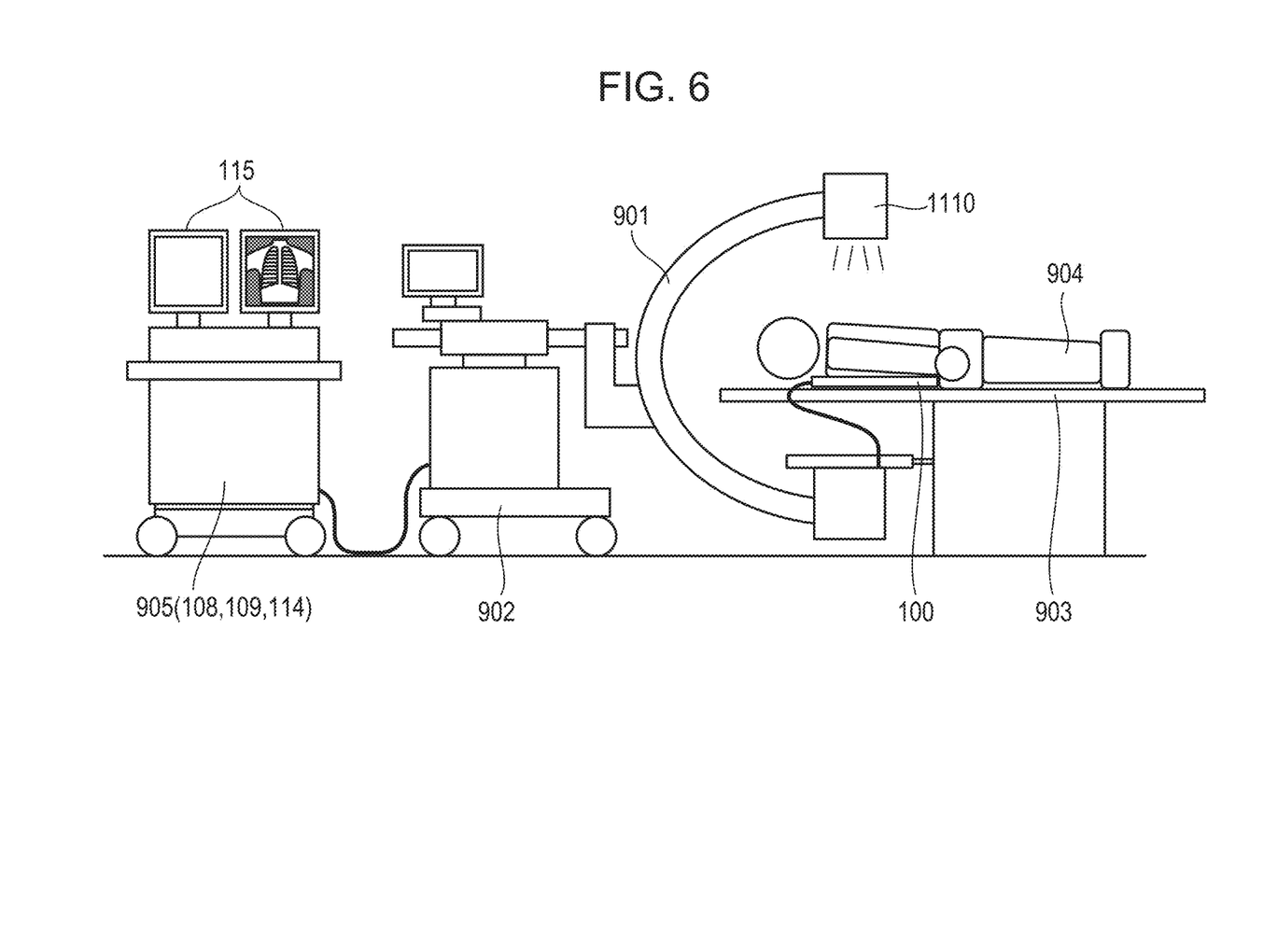
FIG. 6 is a conceptual view of an exemplary application to a radiation detecting system using a radiation detecting device.

The above-described radiation detecting devices may be applied to a radiation detecting system illustrated in FIG. 6. FIG. 6 illustrates an exemplary application to the movable radiation detecting system using the radiation detecting device according to the above-described embodiments.

FIG. 6 is a conceptual view of the radiation detecting system using a transportable radiation detecting device that is capable of taking pictures of moving/still images. In FIG. 6, reference numeral 115 denotes a display that is capable of displaying an image signal acquired from the radiation detecting device 100 according to the embodiment, and reference numeral 903 denotes a bed for placing a test object 904. Reference numeral 902 denotes a car that allows a radiation generating device 1110, the radiation detecting device 100, and a C-type arm 901 to move; and reference numeral 905 denotes a movable controlling device having a structure that allows these to be controlled. The C-type arm 901 holds the radiation generating device 1110 and the radiation detecting device 100. The controlling device 905 includes a control computer 108, a control panel 114, and a radiation controller 109. An image signal acquired by the radiation detecting device 100 can be subjected to image processing and transmitted to, for example, the display device 115. Image data generated by the image processing by the controlling device 905 can be sent to a remote place through transmitting means such as telephone lines. This makes it possible for a doctor at the remote place to diagnose an image based on the transferred image data. It is possible to record the transmitted data image on a film or store the transmitted data image on storage means, such as an optical disk. However, it is possible to form the radiation detecting device 100 so as to be removable from the C-type arm 901 and use a radiation generating device that differs from the radiation generating device 1110 at the C-type arm 901 to take pictures.

Examples using specific materials are described below. With regard to the examples, the results of durability tests described below were good. The durability tests are tests for confirming images by applying radiation to radiation detecting devices after scintillators 120 while disposed so as to face downward have been vibrated at a predetermined frequency and at a gravitational acceleration 2 G.

EXAMPLE 1

For each sensor substrate 112, a monocrystalline silicon substrate having a thickness of 500 μm and provided with a plurality of photodiodes arranged in an array on a first surface 112a is used. The scintillator 120 includes an Al base 121 having a thickness of 300 μm, a CsI:Tl scintillator layer 122 having a thickness of 800 μm, and a polyparaxylylene scintillator protective layer 123 having a thickness of 25 μm. Each sensor substrate 112 is fixed to a base 111 being a glass substrate having a thickness of 1.8 mm by a fixing member 113 using an expanding-and-contracting material 161, which is a polyolefin-based foam having a thickness of 1.5 mm. An adhesive member 130 having a thickness of 25 μm and using an acrylic resin is disposed between the scintillator 120 and the first surfaces 112a of the plurality of sensor substrates 112. As shown in FIG. 2(b), by pressing the adhesive member 130 at a pressure of 0.4 MPa by using the rotatable roller 150, the adhesive member 130 adheres up to locations on side surfaces 112c of the sensor substrates 112 that are 5 μm from sides of the first surfaces 112a.

EXAMPLE 2

Sensor substrates 112, the scintillator 120, and a fixing member 113 that are similar to those according to Example 1 are used. An adhesive member 130 having a thickness of 25 μm and using a hot-melt resin whose main component is ethylene methacrylic acid ester copolymer is disposed between the scintillator 120 and first surfaces 112a of the plurality of sensor substrates 112. As shown in FIG. 2(c), by using the pressure structure 151 heated to a temperature of 100 to 120° C., the adhesive member 130 is pressed at a pressure of 0.4 MPa, so that the adhesive member 130 adheres up to locations on side surfaces 112c of the sensor substrates 112 that are 50 μm from sides of the first surfaces 112a.

EXAMPLE 3

The scintillator 120, an adhesive member 130, and a fixing member 113 that are similar to those according to Example 1 are used. As shown in FIG. 3, sensor substrates 112 are the same as the sensor substrates 112 according Example 1 except that the sensor substrates 112 have a third surface 112d formed as a result of removing corners of a first surface by removing 5 μm of an end of the corresponding first surface. As in Example 1, by using the rotatable roller 150, the adhesive member 130 is pressed at a pressure of 0.4 MPa, so that the adhesive member 130 adheres up to locations on side surfaces 112c of the sensor substrates 112 that are 7 μm from sides of the first surfaces 112a.

EXAMPLE 4

The scintillator 120, an adhesive member 130, and a fixing member 113 that are similar to those according to Example 1 are used. As shown in FIG. 4(b), sensor substrates 112 are the same as the sensor substrates 112 according to Example 1 except that the sensor substrates 112 are inclined towards inner sides of the sensor substrates 112 at the angle D of 1 degree. As in Example 1, by using the rotatable roller 150, the adhesive member 130 is pressed at a pressure of 0.4 MPa, so that the adhesive member 130 adheres up to locations on side surfaces 112c of the sensor substrates 112 that are 4 μm from sides of first surfaces 112a.

The present invention is not limited to the above-described embodiments. Various changes and modifications are possible without departing from the spirit and scope of the present invention. Therefore, the following claims are attached for making public the scope of the present invention.

The invention claimed is:
1. A radiation detecting device comprising:
a plurality of sensor substrates disposed adjacent to each other, each sensor substrate including a first surface where a plurality of photoelectric converting elements are arranged in an array, a second surface that opposes the first surface, and a side surface that connects the first surface and the second surface to each other;
a scintillator disposed at a side of the first surfaces of the plurality of sensor substrates; and
a sheet-like adhesive member for adhering the plurality of sensor substrates and the scintillator to each other,
wherein each of the plurality of sensor substrates further includes a structure having a stepped surface that becomes higher from the side surface in order of the first surface, a guard ring, a passivation film, and a protective layer, the guard ring disposed on at least a portion of the first surface along peripheries of the plurality of photoelectric converting elements, the passivation film that covers a portion of the guard ring and the plurality of photoelectric converting elements, and the protective layer that covers the passivation film except an end portion of the passivation film,
wherein, between the plurality of sensor substrates, the sheet-like adhesive member extends and continuously adheres to the protective layer, the passivation film, the guard ring, the first surfaces and at least portions of the side surfaces such that the sheet-like adhesive member extends and continuously adheres from the structure to the at least portions of the side surfaces.

2. The radiation detecting device according to claim 1, wherein, between the plurality of sensor substrates, at least one of the plurality of sensor substrates includes a third surface that is not parallel to the first surface and to the side surface and that is disposed between the first surface and the side surface, and wherein, between the plurality of sensor substrates, the sheet-like adhesive member extends and continuously adheres from the first surface to the third surface and the at least a portion of the side surface.

3. The radiation detecting device according to either claim 1, wherein, between the plurality of sensor substrates, the side surface of at least one of the plurality of sensor substrates is inclined towards an inner side of the at least one of the sensor substrates from the first surface towards the second surface with respect to a perpendicular line that is perpendicular to the first surface.

4. The radiation detecting device according to any one of claim 1, further comprising: a base that supports the plurality of sensor substrates; and a fixing member for fixing the plurality of sensor substrates to the base, wherein a rigidity of the fixing member is less than a rigidity of the adhesive member.

5. A radiation detecting system comprising:
the radiation detecting device according to claim 1; and
a display device that displays an image based on a signal acquired by the radiation detecting device.

6. A method for manufacturing a radiation detecting device, comprising:
a disposing step of disposing a scintillator at a side of first surfaces of a plurality of sensor substrates with a sheet-like adhesive member interposed therebetween, the plurality of sensor substrates being disposed adjacent to each other, each sensor substrate including the first surface where a plurality of photoelectric converting elements are arranged in an array, a second surface that opposes the first surface, and a side surface that connects the first surface and the second surface to each other; and
an adhering step of causing the sheet-like adhesive member to extend and continuously adhere from the first surfaces to at least portions of the side surfaces between the plurality of sensor substrates by pressing a region of the scintillator corresponding to a region between the plurality of sensor substrates from a side opposite to the plurality of sensor substrates
wherein each of the plurality of sensor substrates further includes a structure having a stepped surface that becomes higher from the side surface in order of the first surface, a guard ring, a passivation film, and a protective layer, the guard ring disposed on at least a portion of the first surface along peripheries of the plurality of photoelectric converting elements, the passivation film that covers a portion of the guard ring and the plurality of photoelectric converting elements, and the protective layer that covers the passivation film except an end portion of the passivation film, and wherein the adhering step comprises causing the sheet-like adhesive member to extend and continuously adhere to the protective layers, the passivation films, the guard rings, the first surfaces, and the at least portions of the side surfaces between the plurality of sensor substrates such that the sheet-like adhesive member extends and continuously adheres from the structure to the at least portions of the side surfaces.

7. The method for manufacturing the radiation detecting device according to claim 6, wherein, between the plurality of sensor substrates, at least one of the plurality of sensor substrates includes a third surface that is not parallel to the first surface and to the side surface and that is disposed between the first surface and the side surface, and wherein the adhering step comprises causing the sheet-like adhesive member to extend and continuously adhere from the first surface to the third surface and the at least a portion of the side surface between the plurality of sensor substrates.

8. The method for manufacturing the radiation detecting device according to claim 6, wherein, between the plurality of sensor substrates, the side surface of at least one of the plurality of sensor substrates is inclined towards an inner side of the at least one of the sensor substrates from the first surface towards the second surface with respect to a perpendicular line that is perpendicular to the first surface.

9. The method for manufacturing the radiation detecting device according to claim 6, further comprising:
a fixing step of fixing the plurality of sensor substrates to a base by using a fixing member,
wherein a rigidity of the fixing member is less than a rigidity of the sheet-like adhesive member.

10. The method for manufacturing the radiation detecting device according to claim 6, wherein the adhering step comprises pressing a region corresponding to a region between the plurality of sensor substrates from the side opposite to the plurality of sensor substrates by using a roller.

* * * * *